(12) United States Patent
Smith et al.

(10) Patent No.: US 8,998,059 B2
(45) Date of Patent: Apr. 7, 2015

(54) ADJUNCT THERAPY DEVICE HAVING DRIVER WITH CAVITY FOR HEMOSTATIC AGENT

(75) Inventors: Craig S. Smith, Cincinnati, OH (US); Gregory B. Blair, San Jose, CA (US); William B. Weisenburgh, II, Maineville, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 837 days.

(21) Appl. No.: 13/195,170

(22) Filed: Aug. 1, 2011

(65) Prior Publication Data

US 2013/0032626 A1 Feb. 7, 2013

(51) Int. Cl.
 *A61B 17/04* (2006.01)
 *A61B 17/072* (2006.01)
 *A61B 17/00* (2006.01)
 *A61B 17/29* (2006.01)

(52) U.S. Cl.
 CPC .  *A61B 17/07207* (2013.01); *A61B 2017/00893* (2013.01); *A61B 2017/07271* (2013.01); *A61B 2017/2927* (2013.01); *A61B 17/00491* (2013.01); *A61B 2017/00889* (2013.01)

(58) Field of Classification Search
 CPC ............... A61B 17/07207; A61B 17/07292; A61B 17/08; A61B 17/085; A61B 17/12186
 USPC ................. 227/176.1; 606/151, 157, 49, 219
 See application file for complete search history.

(56) References Cited

U.S. PATENT DOCUMENTS 2,303,131 A 11/1942 Morgan
3,364,200 A 1/1968 Ashton et al.
3,496,940 A 2/1970 Steinman
3,526,228 A 9/1970 Lyng
4,222,383 A 9/1980 Schossow (Continued)

FOREIGN PATENT DOCUMENTS

CA 481943 2/1947
EP 328 401 8/1989

(Continued)

OTHER PUBLICATIONS

International Search Report dated Mar. 3, 2014 for Application No. PCT/US2012/048766.

(Continued)

*Primary Examiner* — Stephen F Gerrity
*Assistant Examiner* — Joy N Sanders
(74) *Attorney, Agent, or Firm* — Frost Brown Todd LLC

(57) ABSTRACT

An instrument is configured to receive a staple cartridge to staple tissue and expel a fluid from within a container in the staple cartridge. The staple cartridge has an upper deck including staple apertures and orifices formed therein. The orifices are in fluid communication with the containers. The staple cartridge includes staple drivers having a driver body to translate a staple and a container protrusion to expel the fluid out the orifices. The fluid may be expelled while driving the staples out through the staple apertures. The container may be vertically compressible container or, in one alternative, may be a container having a channel and a sealant that is configured to be pierced as the fluid is expelled. Some configurations for the fluid include a hemostatic agent, thrombin, a gel, or a medicament. The containers may also be formed as reservoirs defined within the upper deck and/or cartridge body.

20 Claims, 13 Drawing Sheets

(56) References Cited

U.S. PATENT DOCUMENTS

| | | |
|---|---|---|
| 4,513,746 A | 4/1985 | Aranyi et al. |
| 4,549,545 A | 10/1985 | Levy |
| 4,610,250 A | 9/1986 | Green |
| 4,693,720 A | 9/1987 | Scharnberg et al. |
| 4,805,823 A | 2/1989 | Rothfuss |
| 5,011,493 A | 4/1991 | Belykh et al. |
| 5,064,057 A | 11/1991 | Iwatsuki et al. |
| 5,263,629 A | 11/1993 | Trumbull et al. |
| 5,282,829 A | 2/1994 | Hermes |
| 5,297,324 A | 3/1994 | Su |
| 5,327,914 A | 7/1994 | Shlain |
| 5,366,480 A | 11/1994 | Corriveau et al. |
| 5,383,904 A | 1/1995 | Totakura et al. |
| 5,393,594 A | 2/1995 | Koyfman et al. |
| 5,411,193 A | 5/1995 | Culp |
| 5,415,334 A | 5/1995 | Williamson, IV et al. |
| 5,465,895 A | 11/1995 | Knodel et al. |
| 5,466,462 A | 11/1995 | Rosenthal et al. |
| 5,496,603 A | 3/1996 | Riedel et al. |
| 5,503,638 A | 4/1996 | Cooper et al. |
| 5,542,594 A | 8/1996 | McKean et al. |
| 5,565,210 A | 10/1996 | Rosenthal et al. |
| 5,597,107 A | 1/1997 | Knodel et al. |
| 5,607,590 A | 3/1997 | Shimizu |
| 5,607,686 A | 3/1997 | Totakura et al. |
| 5,632,432 A | 5/1997 | Schulze et al. |
| 5,639,851 A | 6/1997 | Bezwada et al. |
| 5,641,566 A | 6/1997 | Kranzler et al. |
| 5,644,002 A | 7/1997 | Cooper et al. |
| 5,673,840 A | 10/1997 | Schulze et al. |
| 5,690,675 A | 11/1997 | Sawyer et al. |
| 5,704,534 A | 1/1998 | Huitema et al. |
| 5,711,958 A | 1/1998 | Cohn et al. |
| 5,733,308 A | 3/1998 | Daugherty et al. |
| 5,749,968 A | 5/1998 | Melanson et al. |
| 5,752,965 A | 5/1998 | Francis et al. |
| 5,755,778 A | 5/1998 | Kleshinski |
| 5,766,188 A | 6/1998 | Igaki |
| 5,769,892 A | 6/1998 | Kingwell |
| 5,810,855 A | 9/1998 | Rayburn et al. |
| 5,814,055 A | 9/1998 | Knodel et al. |
| 5,814,057 A | 9/1998 | Oi et al. |
| 5,843,096 A | 12/1998 | Igaki et al. |
| 5,902,312 A | 5/1999 | Frater et al. |
| 5,997,895 A | 12/1999 | Narotam et al. |
| 6,019,791 A | 2/2000 | Wood |
| 6,031,148 A | 2/2000 | Hayes et al. |
| 6,099,551 A | 8/2000 | Gabbay |
| 6,174,333 B1 | 1/2001 | Kadiyala et al. |
| 6,203,564 B1 | 3/2001 | Hutton et al. |
| 6,245,081 B1 | 6/2001 | Bowman et al. |
| 6,273,897 B1 | 8/2001 | Dalessandro et al. |
| 6,277,397 B1 | 8/2001 | Shimizu |
| 6,312,474 B1 | 11/2001 | Francis et al. |
| 6,325,810 B1 | 12/2001 | Hamilton et al. |
| 6,355,699 B1 | 3/2002 | Vyakarnam et al. |
| 6,488,197 B1 | 12/2002 | Whitman |
| 6,495,127 B1 | 12/2002 | Wallace et al. |
| 6,511,748 B1 | 1/2003 | Barrows |
| 6,592,597 B2 | 7/2003 | Grant et al. |
| 6,638,285 B2 | 10/2003 | Gabbay |
| 6,656,193 B2 | 12/2003 | Grant et al. |
| 6,704,210 B1 | 3/2004 | Myers |
| 6,814,741 B2 | 11/2004 | Bowman et al. |
| 6,835,336 B2 | 12/2004 | Watt |
| 6,869,436 B2 | 3/2005 | Wendlandt |
| 6,921,412 B1 | 7/2005 | Black et al. |
| 6,962,594 B1 | 11/2005 | Thevenet |
| 6,978,921 B2 | 12/2005 | Shelton, IV et al. |
| 7,000,818 B2 | 2/2006 | Shelton, IV et al. |
| 7,048,755 B2 | 5/2006 | Bonutti et al. |
| 7,084,082 B1 | 8/2006 | Shimizu |
| 7,143,923 B2 | 12/2006 | Shelton, IV et al. |
| 7,147,138 B2 | 12/2006 | Shelton, IV |
| 7,207,471 B2 | 4/2007 | Heinrich et al. |
| 7,211,093 B2 | 5/2007 | Sauer et al. |
| 7,268,205 B2 | 9/2007 | Williams et al. |
| 7,303,108 B2 | 12/2007 | Shelton, IV |
| 7,335,212 B2 | 2/2008 | Edoga et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,517,356 B2 | 4/2009 | Heinrich |
| 7,607,557 B2 | 10/2009 | Shelton, IV et al. |
| 7,721,930 B2 | 5/2010 | McKenna et al. |
| 7,738,971 B2 | 6/2010 | Swayze et al. |
| 7,845,533 B2 | 12/2010 | Marczyk et al. |
| 8,157,830 B2 | 4/2012 | Wenchell |
| 8,215,531 B2 | 7/2012 | Shelton, IV et al. |
| 8,641,730 B2* | 2/2014 | Heeps et al. .................. 606/157 |
| 2002/0165559 A1 | 11/2002 | Grant et al. |
| 2003/0120284 A1 | 6/2003 | Palacios et al. |
| 2003/0183671 A1 | 10/2003 | Mooradian et al. |
| 2004/0093024 A1 | 5/2004 | Lousararian et al. |
| 2004/0167572 A1 | 8/2004 | Roth et al. |
| 2004/0254608 A1 | 12/2004 | Huitema et al. |
| 2005/0042250 A1 | 2/2005 | Damien et al. |
| 2005/0059996 A1 | 3/2005 | Bauman et al. |
| 2005/0070929 A1 | 3/2005 | Dalessandro et al. |
| 2005/0101834 A1 | 5/2005 | Merade |
| 2005/0107810 A1 | 5/2005 | Morales et al. |
| 2005/0145671 A1 | 7/2005 | Viola |
| 2005/0154403 A1 | 7/2005 | Sauer et al. |
| 2005/0245965 A1 | 11/2005 | Orban III et al. |
| 2005/0249772 A1 | 11/2005 | Malaviya et al. |
| 2005/0251153 A1 | 11/2005 | Sakamoto et al. |
| 2005/0283256 A1 | 12/2005 | Sommerich et al. |
| 2005/0288767 A1 | 12/2005 | Kujawski et al. |
| 2006/0004388 A1 | 1/2006 | Whayne et al. |
| 2006/0047312 A1 | 3/2006 | Olmo et al. |
| 2006/0093655 A1 | 5/2006 | Bar et al. |
| 2006/0094318 A1 | 5/2006 | Matsuda et al. |
| 2006/0135992 A1 | 6/2006 | Bettuchi et al. |
| 2006/0173470 A1 | 8/2006 | Oray et al. |
| 2006/0212069 A1 | 9/2006 | Shelton, IV |
| 2006/0229672 A1 | 10/2006 | Forsberg |
| 2006/0265006 A1 | 11/2006 | White et al. |
| 2006/0265007 A1 | 11/2006 | White et al. |
| 2007/0016227 A1 | 1/2007 | de la Torre et al. |
| 2007/0034667 A1 | 2/2007 | Holsten et al. |
| 2007/0034669 A1 | 2/2007 | de la Torre et al. |
| 2007/0049953 A2 | 3/2007 | Shimoji et al. |
| 2007/0060932 A1 | 3/2007 | Stack et al. |
| 2007/0066981 A1 | 3/2007 | Meagher |
| 2007/0112360 A1 | 5/2007 | De Deyne et al. |
| 2007/0128243 A1 | 6/2007 | Serafica et al. |
| 2007/0131732 A1 | 6/2007 | Holsten et al. |
| 2007/0150002 A1 | 6/2007 | Szabo et al. |
| 2007/0156140 A1 | 7/2007 | Baily |
| 2007/0190108 A1 | 8/2007 | Datta et al. |
| 2007/0207180 A1 | 9/2007 | Tanihara et al. |
| 2007/0213522 A1 | 9/2007 | Harris et al. |
| 2007/0219571 A1 | 9/2007 | Balbierz et al. |
| 2007/0225642 A1 | 9/2007 | Houser et al. |
| 2007/0243227 A1 | 10/2007 | Gertner |
| 2007/0246505 A1 | 10/2007 | Pace-Floridia et al. |
| 2007/0286892 A1 | 12/2007 | Herzberg et al. |
| 2008/0039871 A1 | 2/2008 | Wallace et al. |
| 2008/0077131 A1 | 3/2008 | Yates |
| 2008/0078800 A1 | 4/2008 | Hess et al. |
| 2008/0078801 A1 | 4/2008 | Shelton, IV et al. |
| 2008/0078802 A1 | 4/2008 | Hess et al. |
| 2008/0078803 A1 | 4/2008 | Shelton, IV et al. |
| 2008/0078804 A1 | 4/2008 | Shelton, IV et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0081881 A1 | 4/2008 | Swetlin et al. |
| 2008/0082124 A1 | 4/2008 | Hess et al. |
| 2008/0082126 A1 | 4/2008 | Murray et al. |
| 2008/0110959 A1 | 5/2008 | Orban, III et al. |

(56) References Cited

U.S. PATENT DOCUMENTS

| | | | |
|---|---|---|---|
| 2008/0114381 A1 | 5/2008 | Voegele et al. | |
| 2008/0114385 A1 | 5/2008 | Byrum et al. | |
| 2008/0114399 A1 | 5/2008 | Bonutti | |
| 2008/0125812 A1 | 5/2008 | Zubik et al. | |
| 2008/0128469 A1 | 6/2008 | Dalessandro et al. | |
| 2008/0140115 A1 | 6/2008 | Stopek | |
| 2008/0200949 A1 | 8/2008 | Hiles et al. | |
| 2008/0314960 A1 | 12/2008 | Marczyk et al. | |
| 2009/0001122 A1 | 1/2009 | Prommersberger et al. | |
| 2009/0076510 A1 | 3/2009 | Bell et al. | |
| 2009/0118747 A1 | 5/2009 | Bettuchi et al. | |
| 2010/0076429 A1* | 3/2010 | Heinrich | 606/49 |
| 2010/0204641 A1* | 8/2010 | Wenchell | 604/22 |

FOREIGN PATENT DOCUMENTS

| | | |
|---|---|---|
| EP | 0 667 119 | 8/1995 |
| EP | 0 781 564 | 7/1997 |
| EP | 0 818 470 | 1/1998 |
| EP | 1 098 024 | 5/2001 |
| EP | 1 229 841 | 8/2002 |
| EP | 1 494 596 | 1/2005 |
| EP | 1 621 141 | 2/2006 |
| EP | 1 647 286 | 4/2006 |
| EP | 1 759 640 | 3/2007 |
| EP | 1 836 974 | 9/2007 |
| FR | 2 789 885 | 8/2000 |
| FR | 2 850 281 | 7/2004 |
| GB | 222 954 | 10/1924 |
| GB | 493 459 | 10/1938 |
| GB | 913 218 | 12/1962 |
| JP | 107 2740 | 3/1989 |
| JP | 3146773 | 6/1991 |
| JP | 5076586 | 3/1993 |
| JP | 11309151 | 11/1999 |
| WO | WO 93/10731 | 6/1993 |
| WO | WO 98/38923 | 9/1998 |
| WO | WO 01/17446 | 3/2001 |
| WO | WO 02/09593 | 2/2002 |
| WO | WO 02/22184 | 3/2002 |
| WO | WO 03/094743 | 11/2003 |
| WO | WO 2004/060425 | 7/2004 |
| WO | WO 2006/081174 | 8/2006 |
| WO | WO 2006/106269 | 10/2006 |
| WO | WO 2007/067621 | 6/2007 |
| WO | WO 2008/057281 | 5/2008 |

OTHER PUBLICATIONS

Abstract for FR2789885.
Abstract for FR2850281.
Abstract for JP1072740.
Abstract for JP11309151.
Abstract for JP3146773.
Abstract for JP5076586.
International Preliminary Report on Patentability dated Mar. 12, 2014 for Application No. PCT/US2012/048766.

* cited by examiner

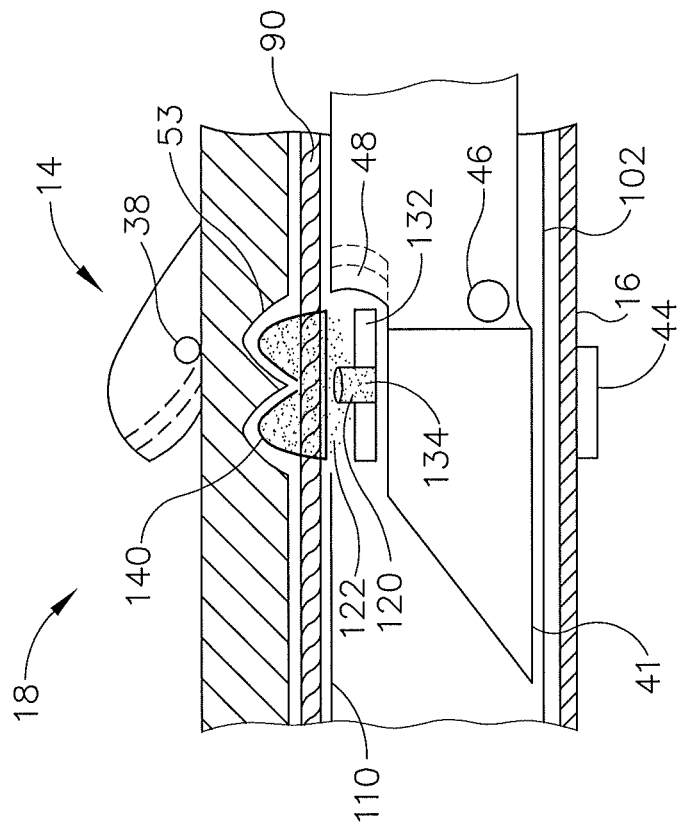
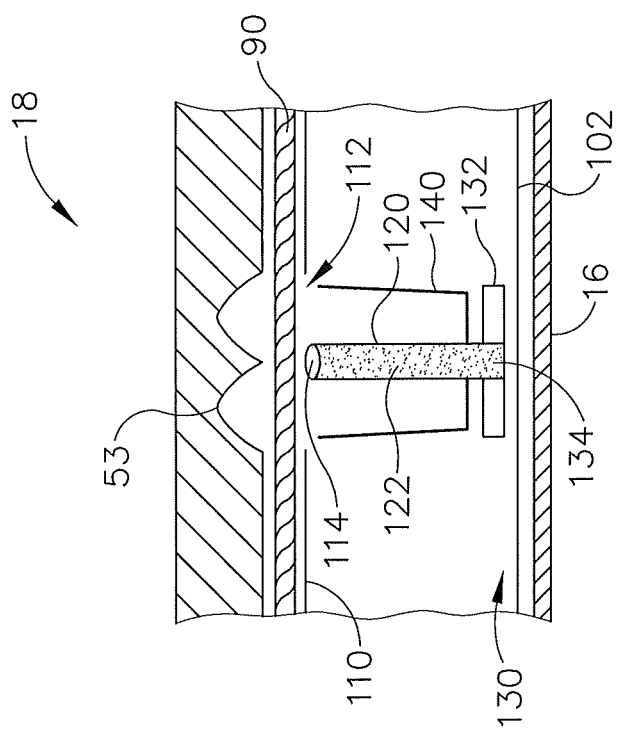

ADJUNCT THERAPY DEVICE HAVING DRIVER WITH CAVITY FOR HEMOSTATIC AGENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 10A depicts a portion of a side cross-sectional view of the staple cartridge of FIG. 7 showing a staple and a fluid in an undeployed state;

FIG. 10B depicts a portion of a side cross-sectional view of the staple cartridge of FIG. 7 showing the staple and fluid deployed by a wedge sled;

Figure 1A:
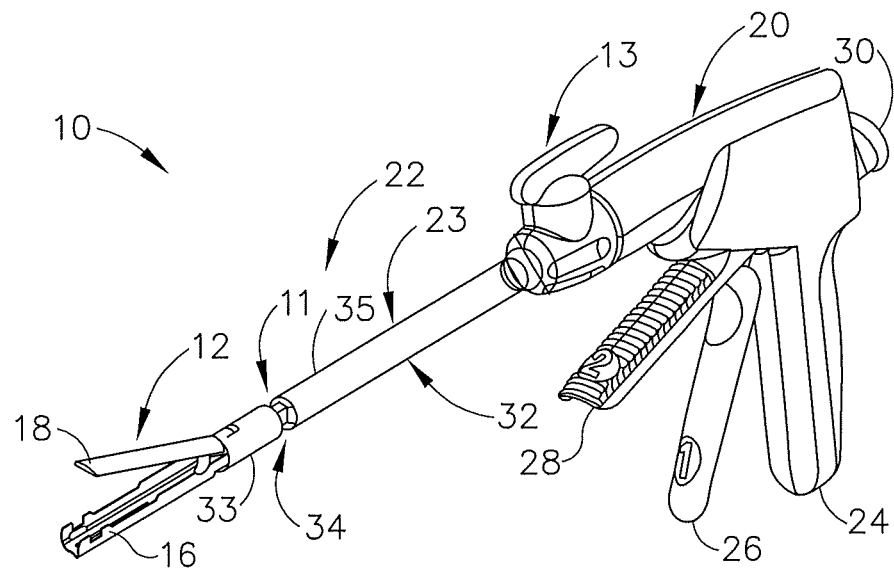
FIG. 1A depicts a perspective view of an articulating surgical instrument with an end effector in a nonarticulated position.
Figure 1B:
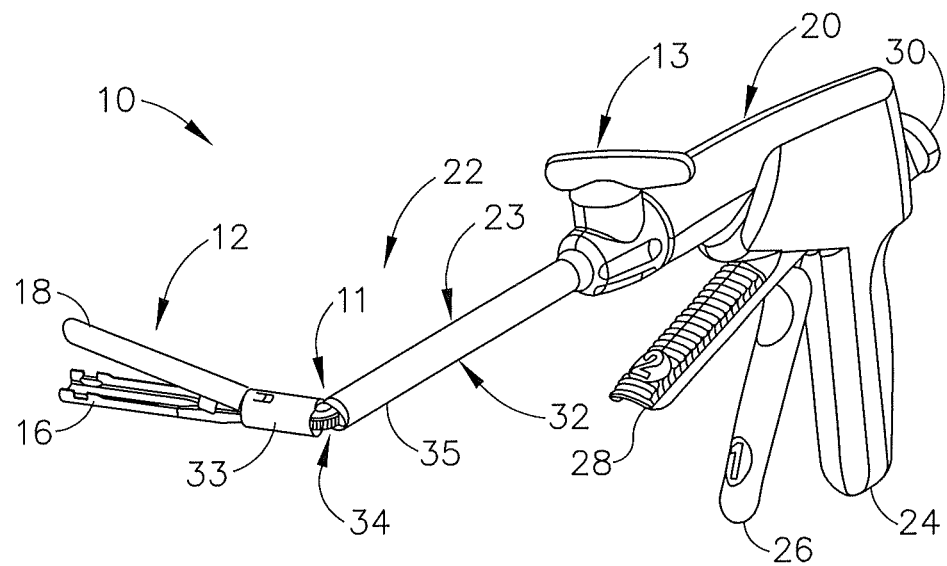
FIG. 1B depicts a perspective view of the surgical instrument of FIG. 1A with an end effector in an articulated position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-6 depict an exemplary surgical stapling and severing instrument (10) that is sized for insertion, in a nonarticulated state as depicted in FIG. 1A, through a trocar cannula passageway to a surgical site in a patient for performing a surgical procedure. Surgical and stapling and severing instrument (10) includes handle portion (20) connected to implement portion (22), the latter further comprising shaft (23) distally terminating in an articulating mechanism (11) and a distally attached end effector (12). Once articulation mechanism (11) and distally end effector (12) are inserted through the cannula passageway of a trocar, articulation mechanism (11) may be remotely articulated, as depicted in FIG. 1B, by articulation control (13). Thereby, end effector (12) may reach behind an organ or approach tissue from a desired angle or for other reasons. It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

End effector (12) of the present example includes a lower jaw (16) and a pivotable anvil (18). Handle portion (20) includes pistol grip (24) toward which closure trigger (26) is pivotally drawn by the clinician to cause clamping, or closing, of the anvil (18) toward lower jaw (16) of end effector (12). Such closing of anvil (18) is provided through an outmost closure sleeve (32), which longitudinally translates relative to handle portion (20) in response to pivoting of closure trigger (26) relative to pistol grip (24). A distal closure ring (33) of closure sleeve (32) is indirectly supported by frame (34) of implement portion (22). At articulation mechanism (11), a proximal closure tube (35) of closure sleeve (32) communicates with the distal portion (closure ring) (33). Frame (34) is flexibly attached to lower jaw (16) via articulation mechanism (11), enabling articulation in a single plane. Frame (34) also longitudinally slidingly supports a firing drive member (not shown) that extends through shaft (23) and communicates a firing motion from firing trigger (28) to firing bar (14). Firing trigger (28) is farther outboard of closure trigger (26) and is pivotally drawn by the clinician to cause the stapling and severing of clamped tissue in end effector (12), as will be described in greater detail below. Thereafter, release button (30) is depressed to release the tissue from end effector (12).

FIGS. 2-5 depict end effector (12) employing an E-beam firing bar (14) to perform a number of functions. As best seen in FIGS. 3A-3B, firing bar (14) includes a transversely oriented upper pin (38), a firing bar cap (44), a transversely oriented middle pin (46), and a distally presented cutting edge (48). Upper pin (38) is positioned and translatable within an anvil pocket (40) of anvil (18). Firing bar cap (44) slidably engages a lower surface of lower jaw (16) by having firing bar (14) extend through channel slot (45) (shown in FIG. 3B) that is formed through lower jaw (16). Middle pin (46) slidingly engages a top surface of lower jaw (16), cooperating with firing bar cap (44). Thereby, firing bar (14) affirmatively spaces end effector (12) during firing, overcoming pinching that may occur between anvil (18) and lower jaw (16) with a minimal amount of clamped tissue and overcoming staple malformation with an excessive amount of clamped tissue.

Figure 2:
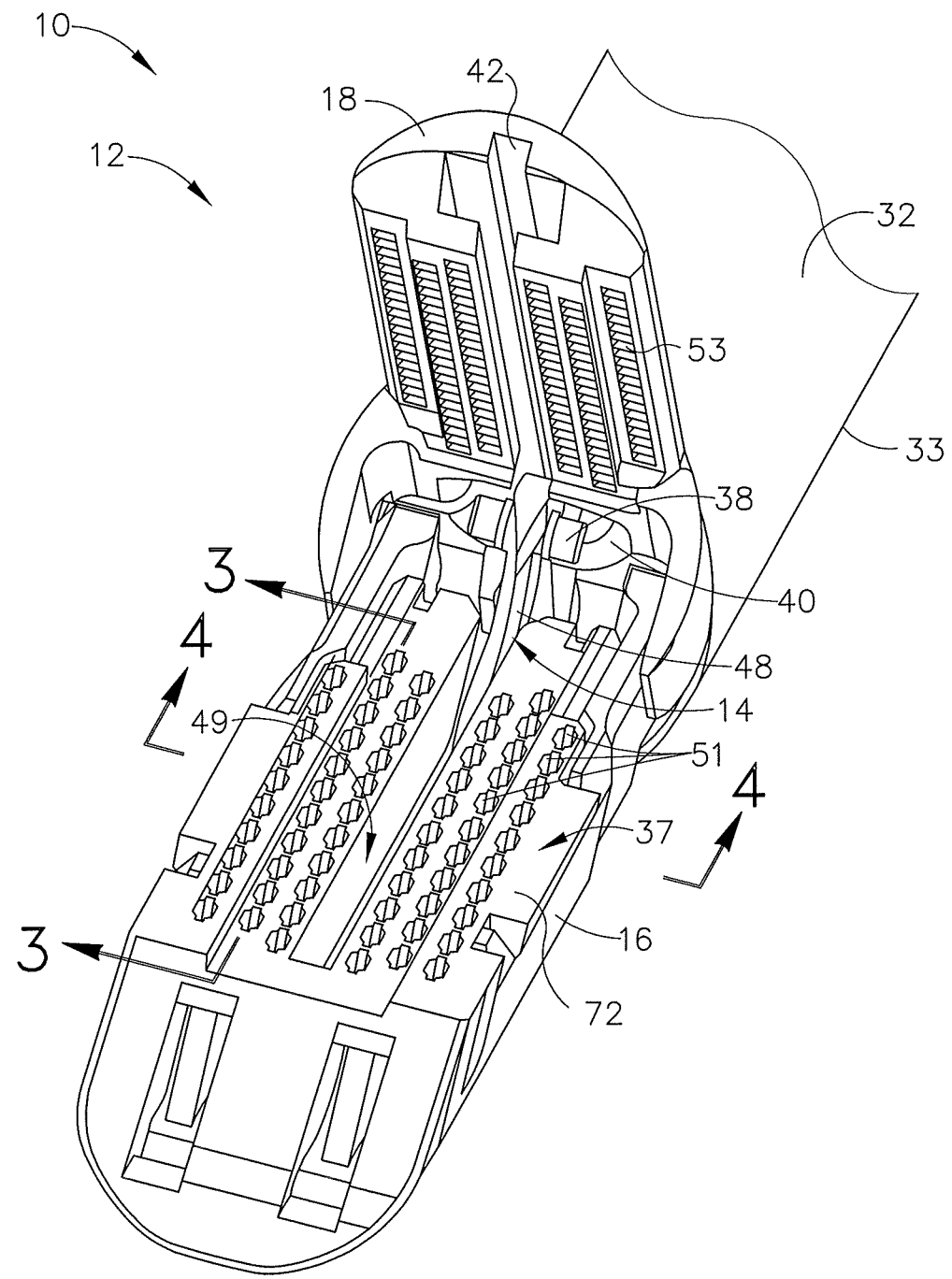
FIG. 2 depicts a perspective view of an opened end effector of the surgical instrument of FIGS. 1A-1B.
Figure 3A:
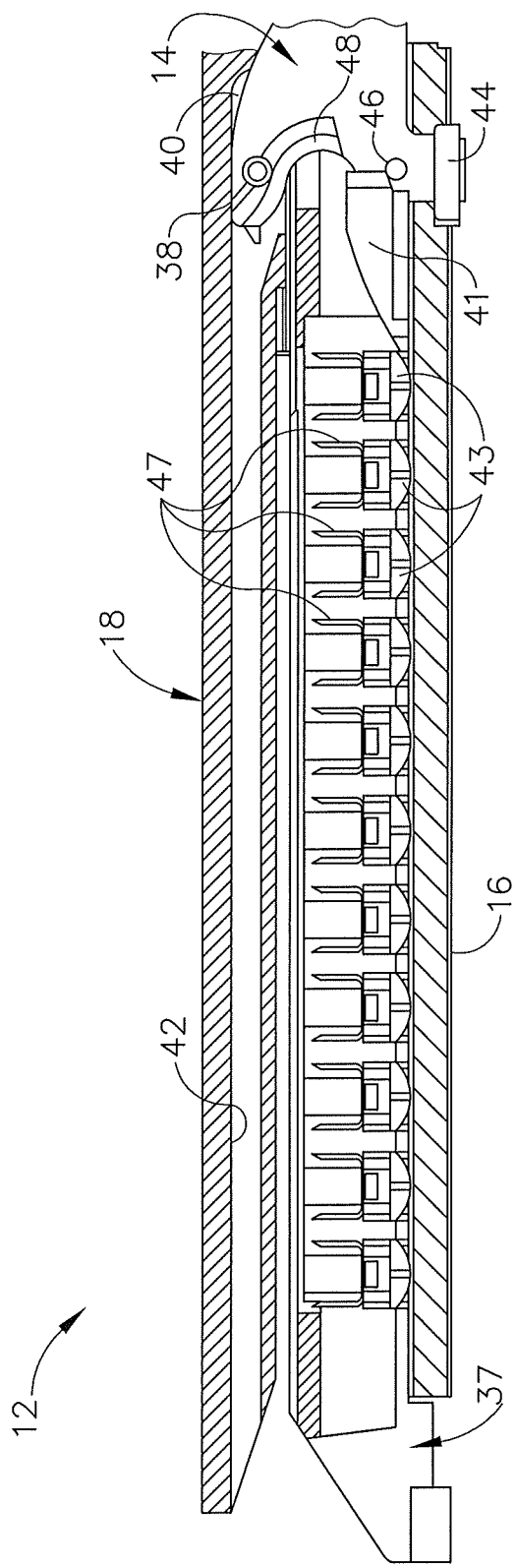
FIG. 3A depicts a side cross-sectional view of the end effector of FIG. 2, taken along line 3-3 of FIG. 2, with the firing bar in a proximal position.
Figure 3B:
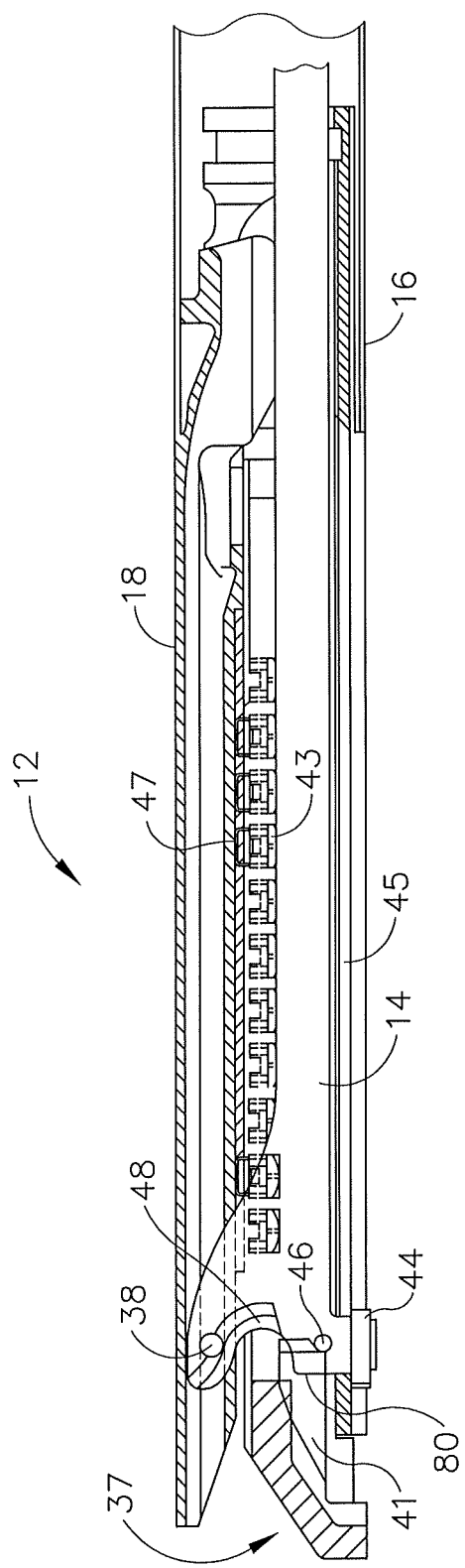
FIG. 3B depicts a side cross-sectional view of the end effector of FIG. 2, taken along line 3-3 of FIG. 2, but showing the firing bar in a distal position.
Figure 4:
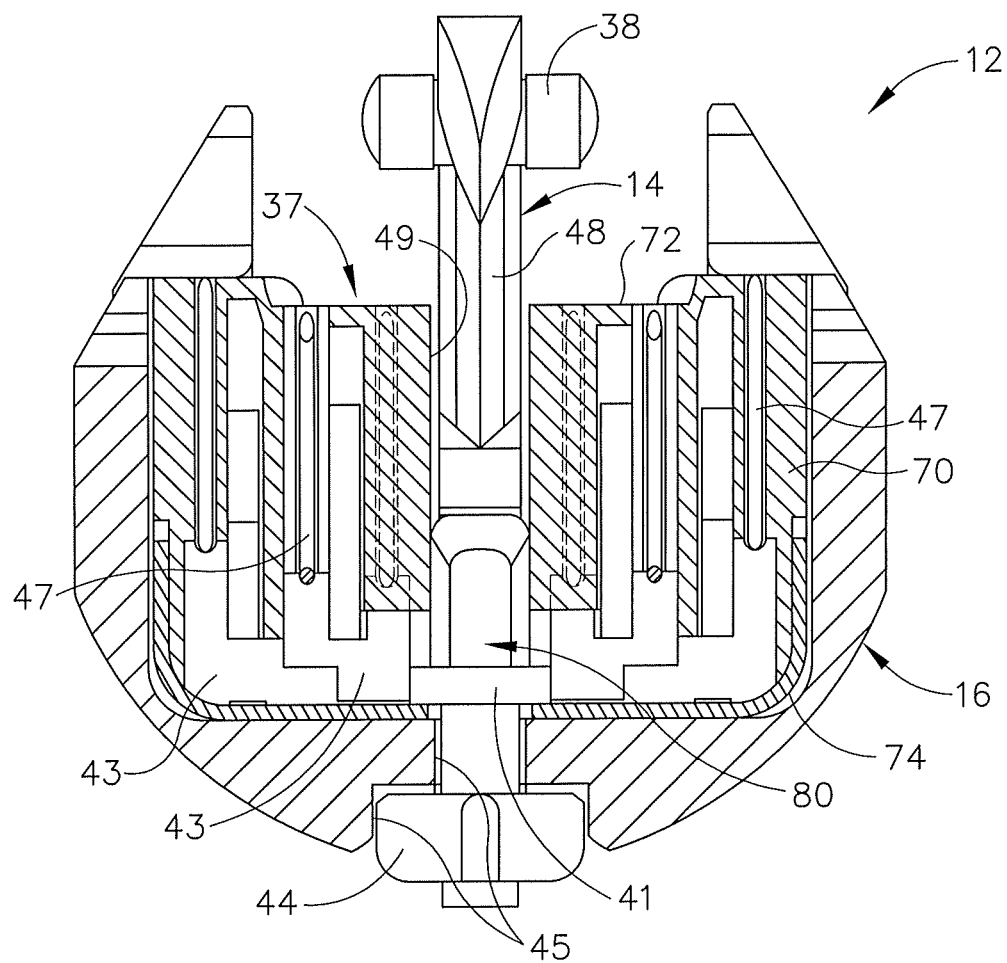
FIG. 4 depicts an end cross-sectional view of the end effector of FIG. 2, taken along line 4-4 of FIG. 2.
Figure 5:
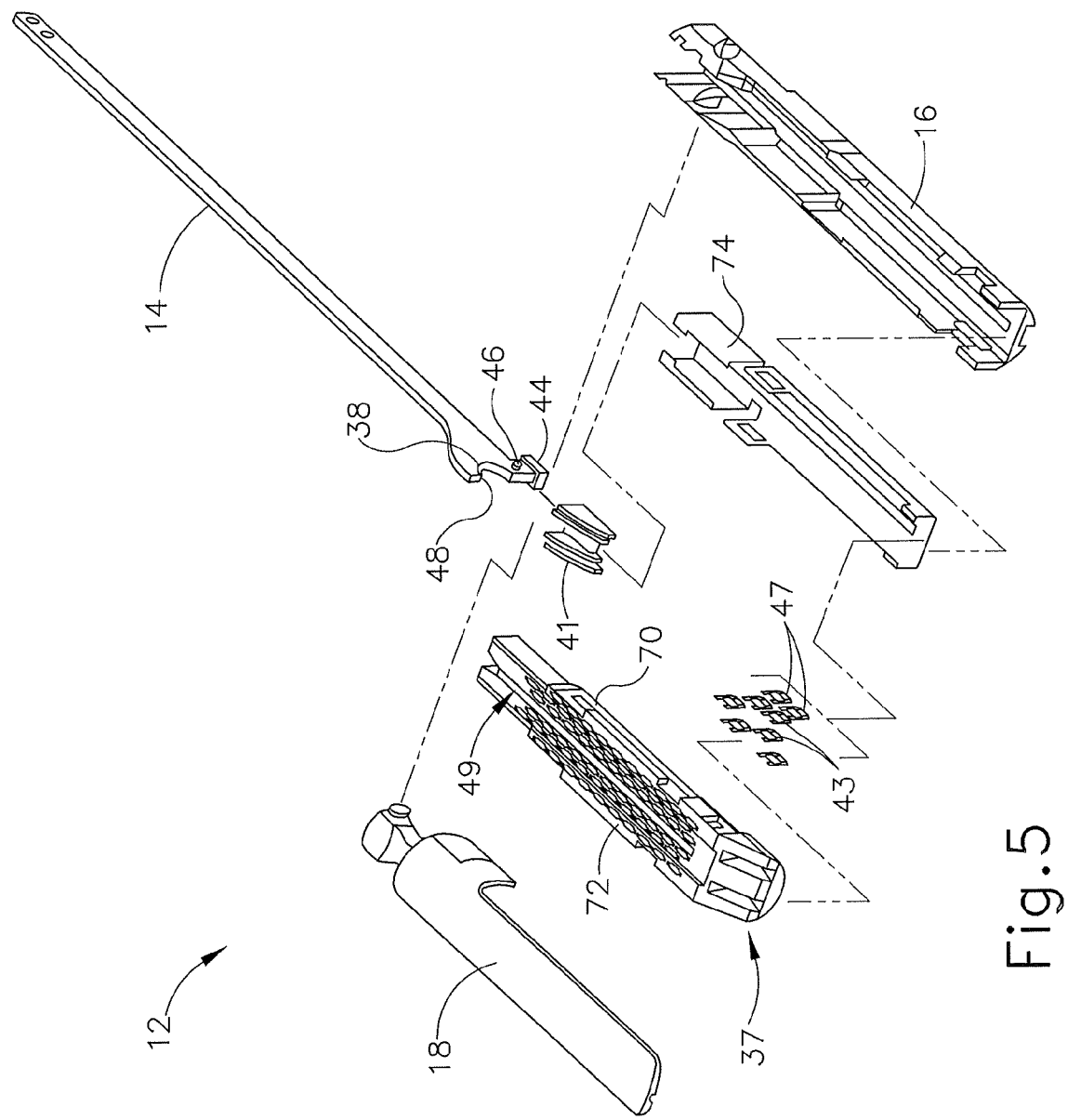
FIG. 5 depicts an exploded perspective view of the end effector of FIG. 2.

FIG. 2 shows firing bar (14) proximally positioned and anvil (18) pivoted to an open position, allowing an unspent staple cartridge (37) to be removably installed into a channel of lower jaw (16). As best seen in FIGS. 4-5, staple cartridge (37) of this example includes a cartridge body (70), which presents an upper deck (72) and is coupled with a lower cartridge tray (74). As best seen in FIG. 2, a vertical slot (49) is formed through part of staple cartridge (37). As also best seen in FIG. 2, three rows of staple apertures (51) are formed through upper deck (72) on one side of vertical slot (49), with another set of three rows of staple apertures (51) being formed through upper deck (72) on the other side of vertical slot (49). Referring back to FIGS. 3-5, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 3A-3B and 5, wedge sled (41) presents inclined cam surfaces that urge staple drivers (43) upwardly as wedge sled (41) is driven distally through staple cartridge (37).

With end effector (12) closed as depicted in FIG. 3A, firing bar (14) is advanced in engagement with anvil (18) by having upper pin (38) enter a longitudinal anvil slot (42). A pusher block (80) is located at the distal end of firing bar (14), and is configured to engage wedge sled (41) such that wedge sled (41) is pushed distally by pusher block (80) as firing bar (14) is advanced distally through staple cartridge (37). During such firing, cutting edge (48) of firing bar (14) enters vertical slot (49) of staple cartridge (37), severing tissue clamped between staple cartridge (37) and anvil (18). As shown in FIGS. 3A-3B, middle pin (46) and pusher block (80) together actuate staple cartridge (37) by entering into a firing slot within staple cartridge (37), driving wedge sled (41) into upward camming contact with staple drivers (43) that in turn drive staples (47) out through staple apertures (51) and into forming contact with staple forming pockets (53) on the inner surface of anvil (18). FIG. 3B depicts firing bar (14) fully distally translated after completing severing and stapling tissue.

Figure 6:
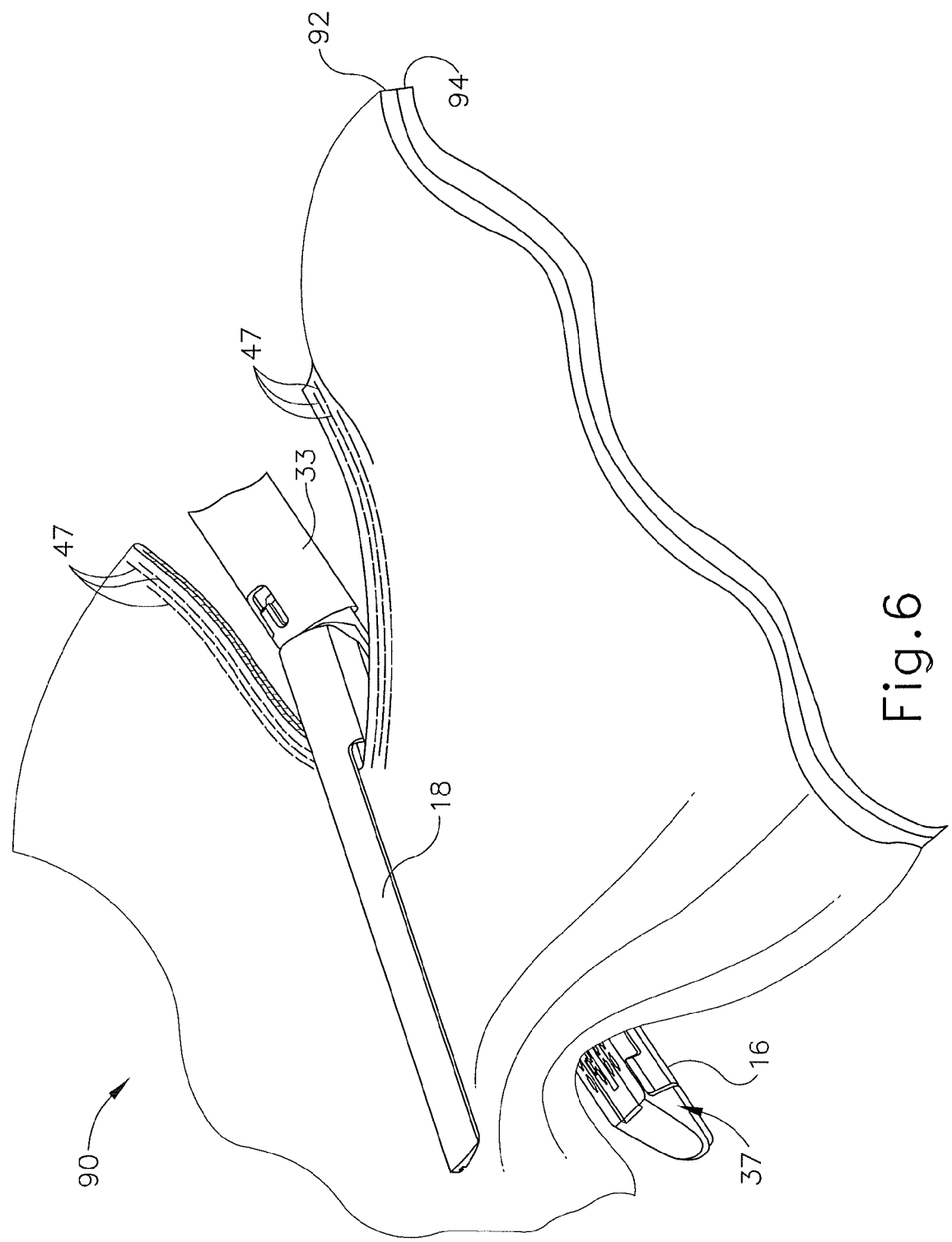
FIG. 6 depicts a perspective view of the end effector of FIG. 2, positioned at tissue and having been actuated once in the tissue.

FIG. 6 shows end effector (12) having been actuated through a single stroke through tissue (90). As shown, cutting edge (48) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 6 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; and/or U.S. Pat. No. 7,721,930. As noted above, the disclosures of each of those patents are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Alternative Staple Cartridge

Figure 7:
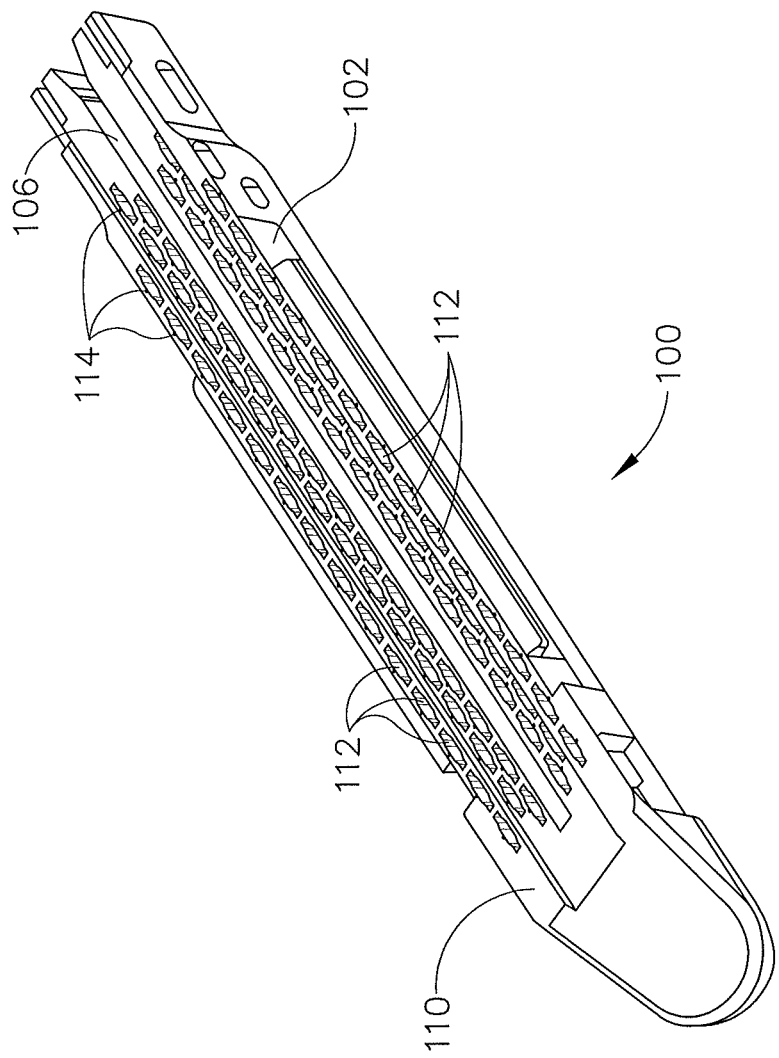
FIG. 7 depicts a perspective view of an exemplary alternative staple cartridge.
Figure 8:
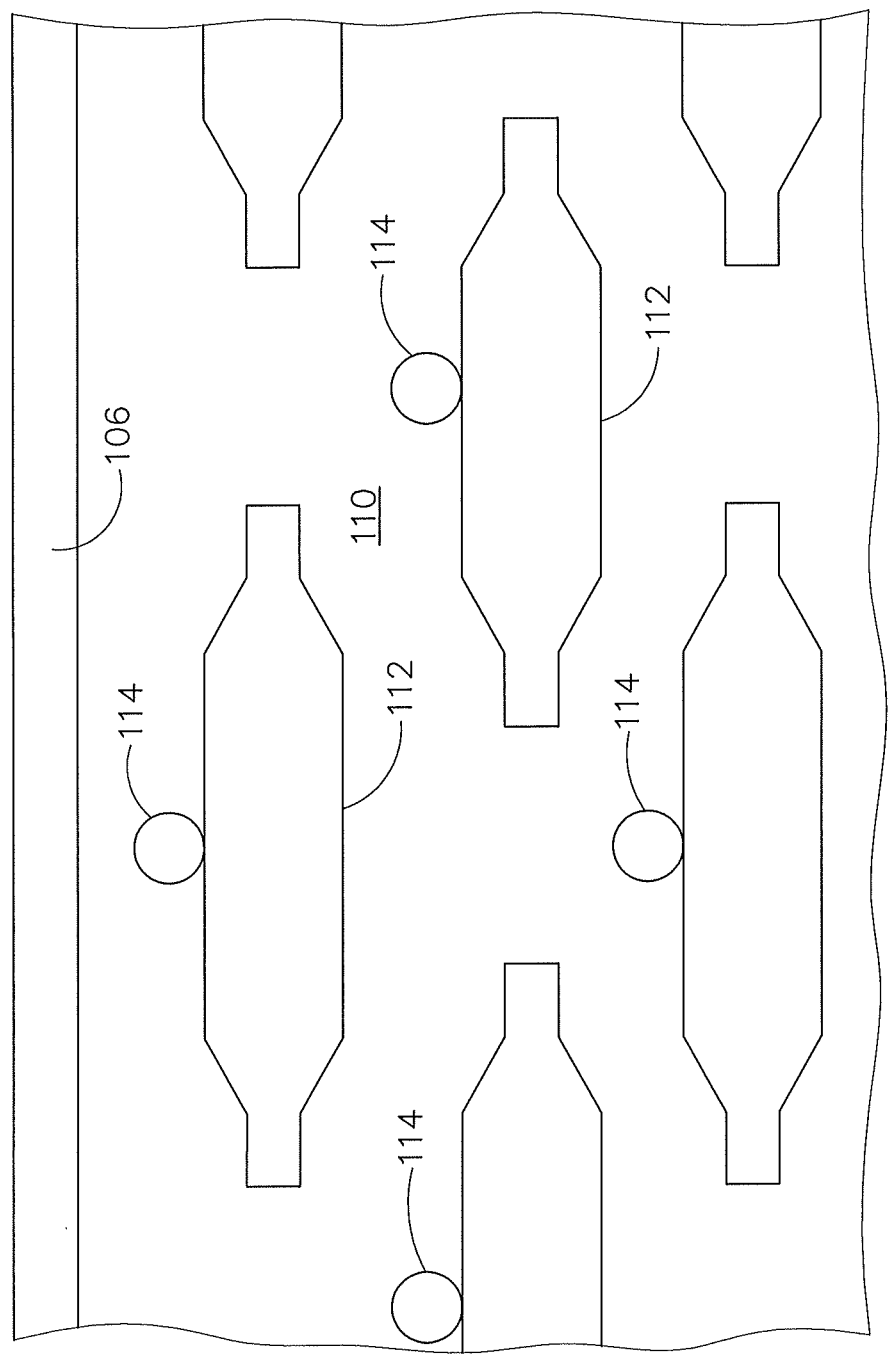
FIG. 8 depicts an enlarged view of an upper deck of the staple cartridge of FIG. 7.

FIG. 7 depicts an exemplary alternative staple cartridge (100). Cartridge (100) of the present example comprises a cartridge body (102) having an upper deck (110). Cartridge (100) may include a cartridge tray, such as cartridge tray (74), but this is merely optional. Upper deck (110) comprises a plurality of staple apertures (112), a plurality of fluid orifices (114), and a vertical slot (106). In the present example, the plurality of staple apertures (112) comprise a first set of three rows of staple apertures (112) that are formed through upper deck (110) on one side of vertical slot (106) and another set of three rows of staple apertures (112) being formed through upper deck (110) on the other side of vertical slot (106). As best seen in FIG. 8, a plurality of fluid orifices (114) also extend through upper deck (110) with one fluid orifice (114) corresponding to each staple aperture (112). Other suitable configurations for upper deck (110) and cartridge (100) will be apparent to one of ordinary skill in the art in view of the teachings herein. For instance, more than one fluid orifice (114) may be provided for each staple aperture (112), or a single fluid orifice (114) may correspond to a group of staple apertures (112). In addition, a plug, such as a bioresorbable plug, may be inserted into orifice (114) or a film may be placed atop orifice (114) to seal orifice (114) prior to use of staple cartridge (100). In the case of a plug, the plug may be forced out when fluid (122) is expelled, as will be described below.

Figure 9:
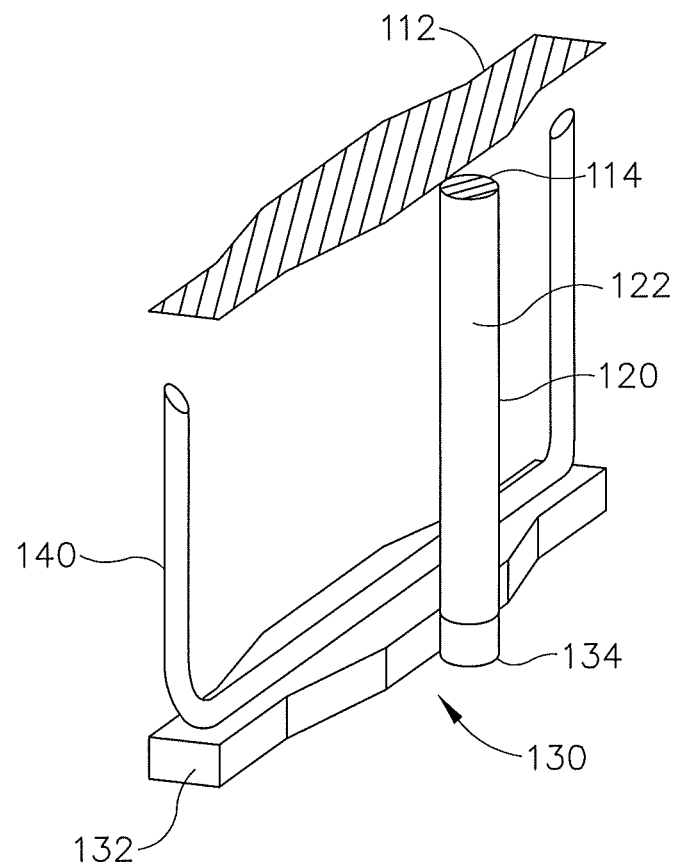
FIG. 9 depicts a perspective view of an exemplary staple aperture with a container, a staple, and a staple driver.

Referring now to FIGS. 9-10B, a container (120) is coupled to each fluid orifice (114) and extends below upper deck (110). Container (120) of the present example comprises a vertically compressible container configured to contain a fluid (122) therein. Merely exemplary fluids (122) that may be used with container (120) include thrombin, lyophilized thrombin (such as that used in Surgiflo® of Ethicon, Inc. in Somerville, N.J.), mussel-based or derived adhesives, platelet poor plasma (PPP) platelet rich plasma (PRP), Chitosan, calcium alginate, fibrin, adhesives, image enhancing agents, necrosing agents, sclerosing agents, coagulants, therapeutic agents, medicaments, analeptic agents, anesthesia agents, antidiuretic agents, analgesic agents, antiseptic agents, antispasmodic agents, cardiac agents, depressant agents, diuretic agents, hemostatic agents, hormonal agents, sedative agents, stimulant agents, vascular agents, time release agents, drugs, absorbable materials, colorants, plasticizing agents, bulking agents, tamponade materials, thixotropic agents, antibacterial agents, buffers, catalysts, fillers, micro particles, thickeners, solvents, natural or synthetic rubbers, stabilizers, pH modifiers, bioactive agents, cross-linking agents, chain transfer agents, fibrous reinforcements, colorants, preservatives, formaldehyde reducing or scavenging agents, and/or any other fluid, including liquids, gels, pastes, etc., suitable to be introduced to tissue. Moreover, components that may be suspended in a liquid, gel, and/or paste may also be used within container (120). Other suitable compounds, materials, substances, etc., that may be used in container (120) will be apparent to one of ordinary skill in the art in view of the teachings herein. Fluid (122) of the present example may be injected into container (120) through orifice (114).

A wedge sled (41), shown in FIG. 10B, and a staple driver (130) are disposed within cartridge body (102), with wedge sled (41) being initially located proximal to staple driver (130). Wedge sled (41) is translatable longitudinally within staple cartridge (100); while staple driver (130) is translatable vertically within staple cartridge (100). Staple driver (130) of the present example comprises a driver body (132) and an integral container protrusion (134). Staples (140) are included within cartridge body (102) and are above a corresponding driver body (132) of staple drivers (130). Each staple (140) is vertically translatable within cartridge body (102) by an associated driver body (132) to drive staple (140) out through a corresponding staple aperture (112). Container protrusion (134) of the present example is configured be in substantial vertical alignment with container (120) such that when staple driver (130) is cammed upward by the longitudinal movement of wedge sled (41), container protrusion (134) contacts and compresses container (120), thereby expelling fluid (122) through orifice (114). As will be appreciated by one skilled in the art, if container (120) is initially in contact with container protrusion (134), fluid (122) may be expelled upon the initial vertical translation of container protrusion (134). In an alternative configuration, container (120)

may be initially not in contact with container protrusion (134), and the vertical displacement between container (120) and container protrusion (134) may provide a timing delay between the initial vertical translation of staple driver (130) and the expulsion of fluid (122).

Referring specifically to FIG. 10A, staple (140) and container (120) having fluid (122) therein are shown in an undeployed state. In the present example, cartridge (100) has been inserted into lower jaw (16) and anvil (18) has been pivoted closed on to tissue (90). Staple (140) is positioned below staple aperture (112) and atop staple driver (130). Container (120) extends downwardly from orifice (114) and contains fluid (122), as described above. Staple driver (130), having staple body (132) and container protrusion (134) may rest atop the bottom of container body (102), or staple driver (130) may be propped up to aid wedge sled (41) in camming staple driver (130) vertically. In one configuration, staple driver (130) may comprise a bottom surface having a complementary wedge to wedge sled (41) such that a top surface of staple driver (130) may be parallel to upper deck (110) as staple driver (130) is vertically cammed by wedge sled (41).

When firing trigger (28), discussed above, is pulled, firing bar (14) and wedge sled (41) translate distally through staple cartridge (100), as shown in FIG. 10B. Specifically, as firing bar (14) advances, middle pin (46) engages wedge sled (41) to slidably translate wedge sled (41) distally. When wedge sled (41) encounters a staple driver (130), wedge sled (41) engages driver body (132) and begins to cam staple driver (130) vertically. As staple driver (130) cams vertically, container protrusion (134) contacts container (120) and begins to vertically compress container (120), thereby forcing fluid (122) out through orifice (114). As staple driver (130) continues to cam upwardly, staple (140) pierces through tissue (90), engages staple forming pocket (53), and deforms according to staple forming pocket (53). Container protrusion (134) may continue to vertically compress container (120) until staple driver (130) is at the peak of wedge sled (41). As can be appreciated by one skilled in the art, in the present configuration fluid (122) expels from orifices (114) as staples (140) staple tissue (90) and cutting edge (48) of firing bar (14) severs tissue (90). If a hemostatic fluid is used as fluid (122), the excretion of fluid (122) may reduce or limit blood loss when severing and stapling tissue. In addition, if a medicinal component is included in fluid (122), inflammation or other tissue conditions may be treated when severing and stapling tissue (90). While one merely exemplary configuration for staple driver (130) and container (120) has been described, other configurations for staple driver (130), container protrusion (134), and/or container (120) will be apparent to one of ordinary skill in the art in view of the teachings herein.

Figure 11:
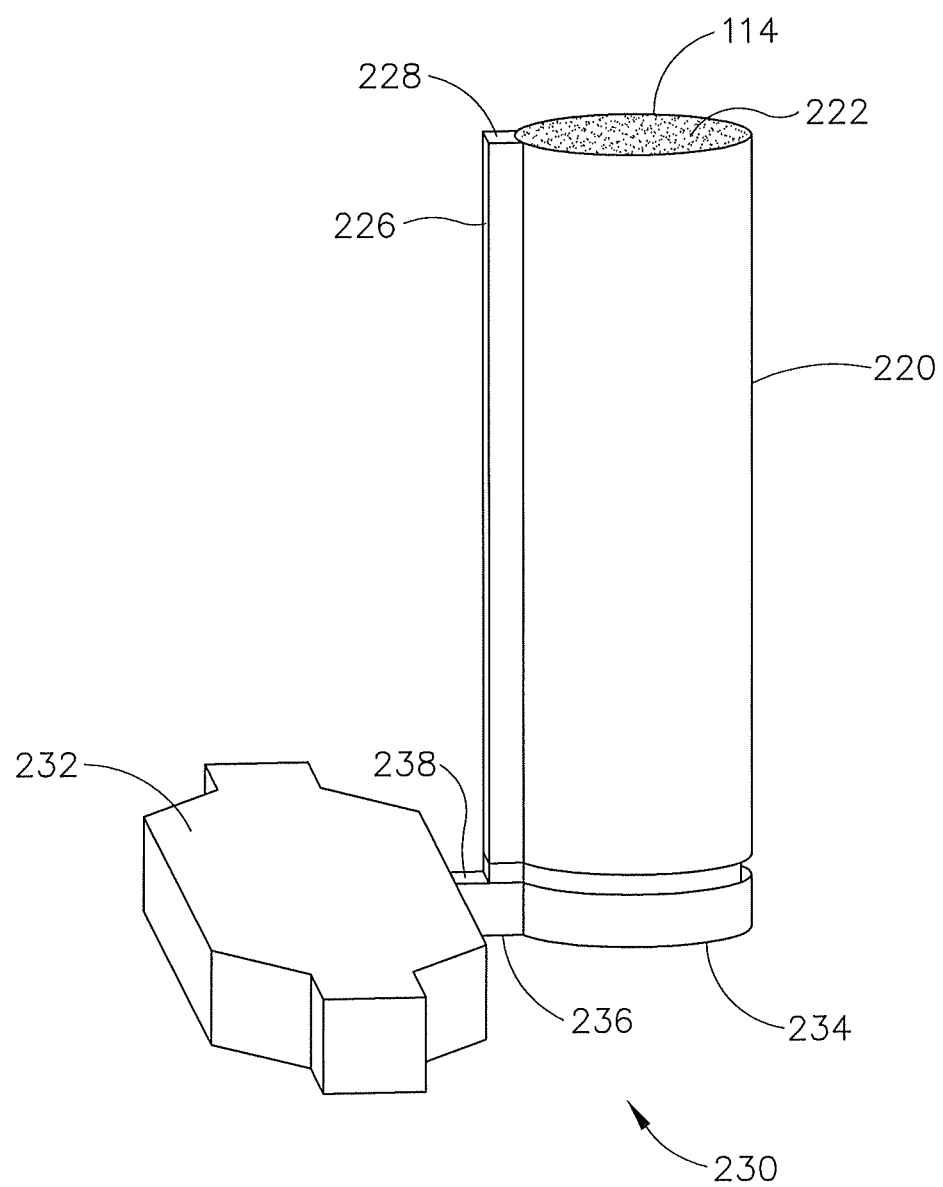
FIG. 11 depicts an alternative configuration for a container and a staple driver.

One such alternative configuration, shown in FIG. 11, has a container (220) that may be a solid container extending downwardly from orifice (114) and having a channel (226) extending vertically along a portion of container (220). In the present example, container (220) is shown as a cylindrical container, but it should be understood that other shapes, sizes, and configurations for container (220) may be used. Indeed, in an alternative configuration, container (220) may be a cavity formed within cartridge body (102) and/or upper deck (112). Additionally, one or more plugs, such as bioresorbable plugs, may be inserted into orifice (114) and/or a portion of container (220), or, alternatively, a film may be laid atop one or more orifices (114) on upper deck (110) of cartridge (100). Channel (226) of the present example may be filled with a pierceable sealant (228), such as RTV, silicone, or other semi-solid, flexible, or pierceable sealants. Sealant (228) substantially fluidly seals channel (226) such that container (220) may be filled with a fluid (222) without substantially leaking through channel (226). Fluid (222) of the present example may be injected into container (220) through orifice (114) or from the bottom of container (220) prior to inserting container protrusion (234), as described below.

As shown in the present example, staple driver (230) comprises a driver body (232) configured to vertically translate a staple, a piercing portion (236) extending from driver body (232), and a container protrusion (234) configured to vertically slide within container (220) to force fluid (222) out orifice (114). Container protrusion (234) may be configured in a substantially similar manner to a syringe plunger, such as including one or more seals (not shown) disposed about container protrusion (234) to prevent fluid (222) from leaking around container protrusion (234). Piercing portion (236) comprises a cutter portion (238) that is configured to pierce sealant (228) as staple driver (230) is cammed vertically. Thus, container protrusion (234) may vertically translate within container (220) to force out fluid (222) while piercing portion (236) couples container protrusion (234) to driver body (232) and cutter portion (238) pierces sealant (226). The pressure of fluid (222) when container protrusion (234) translates vertically may be sufficient to "pop out" the one or more bioresorbable plugs noted previously. Accordingly, fluid (222) may be delivered to tissue (90) and/or staple (140) via this additional configuration. While container protrusion (234) is shown as substantially planar with driver body (232), container protrusion (234) may alternatively be offset, above or below, driver body (232).

Figure 12:
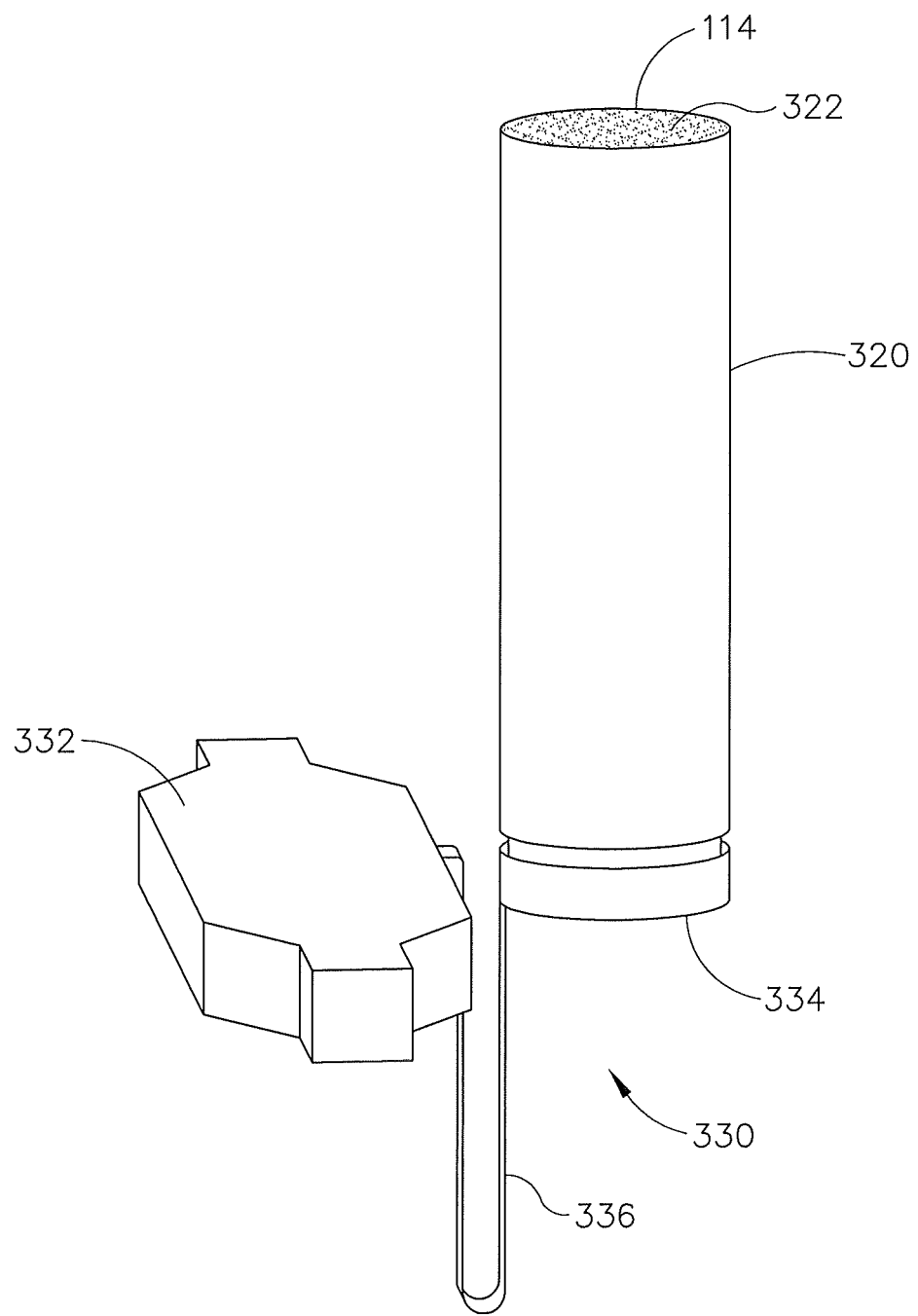
FIG. 12 depicts yet another alternative configuration for a container and a staple driver.

In another configuration shown in FIG. 12, staple driver (330) includes an elongate vertical U-shaped portion (336) coupling container protrusion (334) to driver body (332). The vertical dimensioning of U-shaped portion (336) may be such that container protrusion (334) may slidably translate within a solid container (320) to expel fluid (322) out orifice (114) without the bottom of U-shaped portion (336) contacting the lower edge of container (320). Alternatively, the bottom of U-shaped portion (336) may contact container (320) when staple driver (330) is at the apex, or U-shaped portion (336) may be configured to break-away at a predetermined position when expelling fluid (322) and driving a staple with staple driver (330). Still other suitable configurations for staple drivers and containers will be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) an instrument comprising:
      i. a handle portion,
      ii. an end effector extending proximally from the handle portion; and
   (b) a staple cartridge insertable into the end effector, the staple cartridge comprising:
      i. a cartridge body having an upper deck, the upper deck comprising:
         (1) a vertical slot formed in the upper deck and extending longitudinally from a proximal end of the upper deck,
         (2) a plurality of staple apertures, and
         (3) a plurality of orifices,
      ii. a plurality of staple drivers, wherein each staple driver comprises a container protrusion,
      iii. a plurality of staples disposed above the plurality of staple drivers, wherein the plurality of staples and the plurality of staple drivers are vertically translatable relative to the cartridge body,
      iv. a plurality of containers disposed within the cartridge body, each container of the plurality of containers having an end in fluid communication with an orifice of the plurality of orifices, and
      v. a fluid disposed within each container of the plurality of containers.

2. The apparatus of claim 1 wherein each staple driver of the plurality of staple drivers is configured to drive a staple of the plurality of staples out through a staple aperture of the plurality of staple apertures while concurrently expelling the fluid in a container of the plurality of containers out through an orifice of the plurality of orifices.

3. The apparatus of claim 1 wherein the plurality of containers each comprise a vertically compressible portion.

4. The apparatus of claim 3 wherein the container protrusion is operable to compress a container of the plurality of containers.

5. The apparatus of claim 1 wherein each staple driver is in substantial vertical alignment with one staple aperture and one orifice.

6. The apparatus of claim 1 wherein each container of the plurality of containers comprises:
   (1) a vertical channel interposed between the corresponding staple aperture and the container, and
   (2) a sealant disposed within the channel.

7. The apparatus of claim 6 wherein each staple driver of the plurality of staple drivers comprises a respective piercing portion, wherein the piercing portion is operable to pierce the sealant disposed within the channel of an associated container of the plurality of containers.

8. The apparatus of claim 6 wherein the container protrusion is operable to slidably translate within the container of the plurality of containers.

9. The apparatus of claim 1 wherein the plurality of containers are formed within the cartridge body.

10. The apparatus of claim 1 wherein the plurality of containers are discrete relative to each other.

11. The apparatus of claim 1 wherein the fluid comprises a hemostatic agent.

12. The apparatus of claim 1 wherein the fluid comprises thrombin.

13. The apparatus of claim 1 wherein the fluid comprises a gel.

14. The apparatus of claim 1 wherein the fluid comprises a medicament.

15. The apparatus of claim 1 wherein the end effector comprises a firing bar having a cutting edge, and wherein the vertical slot of the upper deck is configured to permit the cutting edge to longitudinally translate along the vertical slot.

16. An apparatus for endosurgical use, the apparatus comprising:
   (a) a cartridge body having an upper deck, the upper deck comprising: i. a plurality of staple apertures, and ii. a plurality of orifices;
   (b) a staple driver vertically translatable relative to the cartridge body, wherein each staple driver comprises a container protrusion;
   (c) a plurality of staples, wherein the plurality of staples are vertically translatable relative to the cartridge body;
   (d) a plurality of containers, each container being in fluid communication with a respective orifice of the plurality of orifices, wherein each container protrusion is operable to expel fluid out of a corresponding container of the plurality of containers; and
   (e) a fluid disposed within each of the plurality of containers.

17. The apparatus of claim 16 wherein the container protrusion of each staple driver is slidably disposed within the corresponding container of the plurality of containers.

18. The apparatus of claim 16 wherein the staple driver is configured to drive a staple of the plurality of staples out through a staple aperture of the plurality of staple apertures while concurrently forcing the fluid in a container of the plurality of containers out through an orifice of the plurality of orifices.

19. A method for expelling a fluid from a staple cartridge using an instrument and a staple cartridge; wherein the instrument includes an end effector configured to receive a staple cartridge, the end effector having a staple forming pocket, wherein the staple cartridge includes an upper deck having a staple aperture and an orifice formed therethrough; a container in fluid communication with the orifice; a fluid disposed within the container; a staple driver disposed within the staple cartridge and below the upper deck, the staple driver comprising a driver body and a container protrusion, the container protrusion slidably translatable within the container; and a staple translatable by the staple driver, the method comprising:

(a) inserting the staple cartridge into the end effector;
(b) translating the staple driver and the staple in a substantially vertical direction;
(c) driving the staple through the staple aperture and into the staple forming pocket; and
(d) expelling the fluid out of the container by slidably translating the container protrusion within the container.

20. The method of claim 19 wherein the steps of driving the staple through the staple aperture and into the staple forming pocket and expelling the fluid out of the container by slidably translating the container protrusion within the container are concurrent.

\* \* \* \* \*